United States Patent
Voipio et al.

(10) Patent No.: US 8,182,748 B2
(45) Date of Patent: May 22, 2012

(54) METHOD AND ARRANGEMENT OF MEASURING ACIDITY OR OTHER CHEMICAL OR PHYSICAL PROPERTY OF A GAS

(75) Inventors: Ville Voipio, Helsinki (FI); Katri Vuokila, Vantaa (FI)

(73) Assignee: Janesko Oy, Vantaa (FI)

( * ) Notice: Subject to any disclaimer, the term of this patent is extended or adjusted under 35 U.S.C. 154(b) by 751 days.

(21) Appl. No.: 12/073,657

(22) Filed: Mar. 7, 2008

(65) Prior Publication Data

US 2008/0227215 A1 Sep. 18, 2008

(30) Foreign Application Priority Data

Mar. 16, 2007 (EP) .................................... 07104333

(51) Int. Cl.
*G01N 21/78* (2006.01)
(52) U.S. Cl. .................... 422/82.05; 422/88; 422/82.06; 422/82.07; 422/82.08; 422/164; 436/169; 356/446; 356/445; 356/234; 356/432; 356/436; 356/409; 356/300; 356/326; 356/450
(58) Field of Classification Search .................... 422/88, 422/820.05, 82.06, 82.07, 82.08, 164, 82.11; 436/169; 356/446, 445, 234, 432, 436, 409, 356/300, 326, 346, 450
See application file for complete search history.

(56) References Cited

U.S. PATENT DOCUMENTS

| | | | | |
|---|---|---|---|---|
| 5,120,131 A | * | 6/1992 | Lukosz | 356/481 |
| 5,268,145 A | * | 12/1993 | Namba et al. | 436/169 |
| 5,577,137 A | * | 11/1996 | Groger et al. | 422/68.1 |
| 6,208,423 B1 | * | 3/2001 | Voipio et al. | 356/446 |
| 6,947,138 B2 | | 9/2005 | Arno | |
| 2003/0109055 A1 | * | 6/2003 | Lehmann et al. | 436/164 |
| 2006/0263257 A1 | * | 11/2006 | Beauchamp et al. | 422/88 |
| 2008/0233008 A1 | * | 9/2008 | Sarkisov et al. | 422/82.05 |

FOREIGN PATENT DOCUMENTS

| | | |
|---|---|---|
| EP | 0 244 394 A2 | 11/1987 |
| JP | 4-221746 A | 8/1992 |
| WO | WO 2004/077035 A1 | 9/2004 |

OTHER PUBLICATIONS

European Search Report dated Aug. 13, 2007.
Brinker et al., "Sol-Gel Science, The Physics and Chemistry of Sol-Gel Processing" Academic Press Inc., 1990, pp. 1-13, 788-789 and 794-797.

\* cited by examiner

*Primary Examiner* — In Suk Bullock
*Assistant Examiner* — Sharon Pregler
(74) *Attorney, Agent, or Firm* — Buachanan Ingersoll & Rooney PC

(57) ABSTRACT

A method and an arrangement of measuring acidity or other chemical or physical property of a gas. The invention comprises a membrane having optical indicator molecules bound to a microporous matrix arranged to be placed into contact with the gas to be measured, the optical indicator molecules changing their colour in response to the acidity or other chemical or physical property of the gas, a light source, and a detector. The light source is arranged to emit and direct light to the membrane, the light being transmitted through the membrane, whereby a part of the light is absorbed into the optical indicator molecules, and the rest of the light emitted is guided to the detector, where it is measured.

10 Claims, 1 Drawing Sheet

Figure 1:
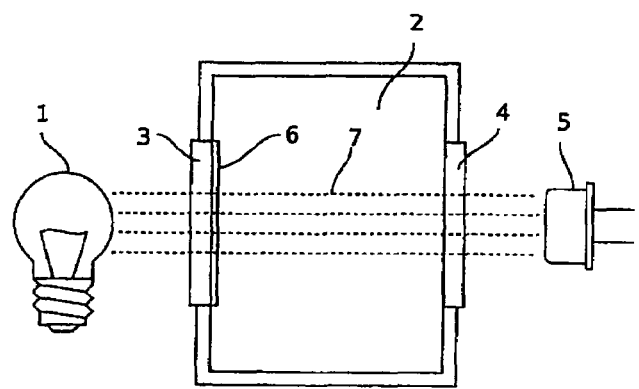

METHOD AND ARRANGEMENT OF MEASURING ACIDITY OR OTHER CHEMICAL OR PHYSICAL PROPERTY OF A GAS

The invention relates to a method and an arrangement of measuring acidity or other chemical or physical property of a gas.

There are several well-known and widely used methods to measure the acidity (pH value) of a liquid. pH measurement is one of the most important measurements in laboratories and chemical industry, and its applications range from heavy industry to microanalytical measurements in biology. Numerous pH measurement instruments are commercially available using glass electrode sensors or semiconductor-based ISFET sensors.

While the liquid acidity measurement technology is well-established, there is also a need to measure the acidity of gases. An example of this use is the measurement of acidity of flue gases, where sulfur dioxide is often present. When sulfur dioxide is dissolved into water, sulfuric acid results.

There are no known methods to measure the acidity directly from a gas. Instead, the gas is in the prior art first dissolved into water, and then the pH value of the water is measured. If the amounts of water and gas are known, and the extent to which the gas dissolves into water is known, the acidity of the gas can be determined.

In practice, this method is error-prone in many applications. With the flue gas application the gas may be fed through water in a wet gas scrubber. The acidity of the scrubber water is then monitored. If there is an emission peak, the scrubber will not be able to dissolve all acidity from the flue gas, and the acidity of the water does not give a true image of the acidity of the gas.

The electrochemical pH sensors commonly used in aqueous applications cannot be used in gas applications, as these sensors require the medium to be conductive and gases are practically complete electric insulators. Also, the measurement principle of these sensors requires a thin liquid layer to be present on their surface.

The object of the invention is to create a simple method and arrangement by which acidity or other chemical or physical property of a gas can be measured. This is obtained with the invention. The basic idea in the invention is to use optical indicator molecules, which change their colour in response, for example to the acidity of the environment. In this case the colour of each indicator molecule depends on the molecular-level interactions it has with the molecules in its immediate vicinity. If indicator molecules are exposed to a gas, their colour is determined by the acidity of the said gas. The method of the invention is characterized in that the method comprises the following steps, arranging a membrane having optical indicator molecules bound to a microporous matrix is placed into contact with the gas to be measured, the optical indicator molecules changing their colour in response to the acidity or other chemical or physical property of the gas, and directing light to the membrane, whereby a part of the light is absorbed into the optical indicator molecules, and measuring the light passed through the membrane. The arrangement of the invention is characterized in that the arrangement comprises, a membrane having optical indicator molecules bound to a microporous matrix arranged to be placed into contact with the gas to be measured, the optical indicator molecules changing their colour in response to the acidity or other chemical or physical property of the gas, a light source, and a detector, the light source being arranged to emit and direct light to the membrane, the light being transmitted through the membrane, whereby a part of the light is absorbed into the optical indicator molecules, and the rest of the light emitted is guided to the detector, where it is measured.

The main advantage of the invention is its simplicity, which makes the introduction and use of the invention advantageous. Another advantage of the invention is that the measurement can be automated in an advantageous manner.

Figure 2:
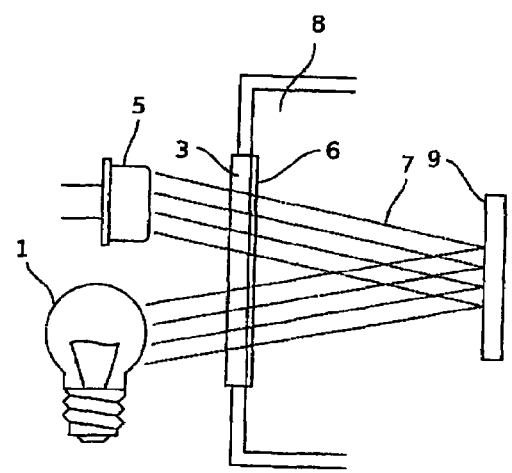
Figure 3:
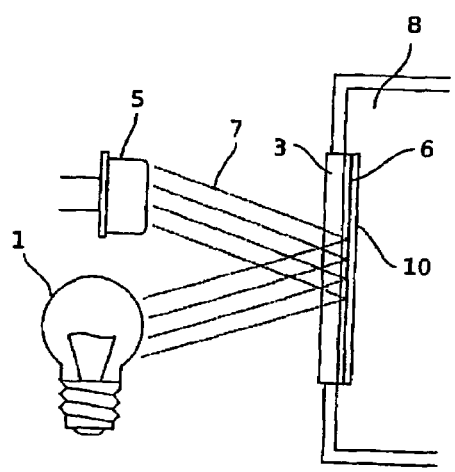
Figure 4:
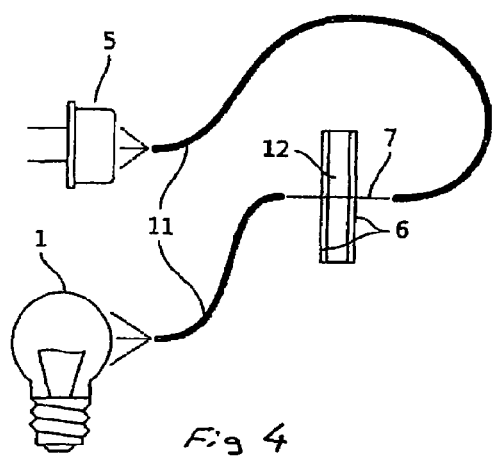

In the following the invention will be described by means of embodiments shown in the attached drawing, whereby FIG. 1 shows a first embodiment of the arrangement of the invention, FIG. 2 shows a second embodiment of the arrangement of the invention, FIG. 3 shows a third embodiment of the arrangement of the invention, and FIG. 4 shows a fourth embodiment of the arrangement of the invention.

The basic thing in the present invention is to use optical indicators, i.e. indicator dyes. As told above one of the advantages of the invention is its simplicity. Despite the simplicity of the basic principle, there are practical challenges associated with this approach. Most indicator dyes are crystalline solids in their pure form. As only the surface of the crystal may interact with the atmosphere surrounding it, only a small fraction of the molecules exhibit a colour change. This can be changed by, e.g., grinding the crystals to a very fine powder, but keeping this powder thinly spread and stationary in a flow of gas is very difficult.

If however the indicator molecules are bound to a microporous membrane matrix, the resulting structure fulfills the requirement of large exposed surface area and yet keeps the molecules stationary. The microporous membrane can advantageously be deposited on a substrate. This basic thought is used in the invention.

There are several methods for making such microporous structures, the most well-known being the Sol-Gel method. In the Sol-Gel method glass is manufactured at low temperatures by using a polymerization reaction. This method allows for tailoring the porosity and pore size of the membrane, and it is possible to use different chemical compositions of the membrane. The Sol-Gel method is described in more detail for instance in the book Sol-Gel Science, The Physics and Chemistry of Sol-Gel Processing, Academic Press, Inc. 1990. A Sol-Gel solution, i.e. a sol, is a colloid solution, which forms an inorganic polymer, glass, when drying on a glass surface. The glass sheet is coated for instance by immersing the sheet into the sol. In this connection a reference is made also to U.S. Pat. No. 6,208,423 B1 describing principally the Sol-Gel method.

Thus, a sensor capable of direct measurement of gas acidity can be constructed by using indicator dye bound into a porous membrane.

In FIG. 1, a gas acidity measurement sensor is shown. The construction has a light source 1, a flow cell 2 having the gas to be measured inside, two optical windows to the flow cell 3, 4, and a detector 5. One of the process windows 3 is coated with a microporous acidity indicator membrane or film 6, i.e. the window 3 acts as a substrate on which the microporous acidity indicator membrane or film 6 is deposited.

Light 7 emitted from the light source 1 goes through the window 3 essentially unchanged. After passing through the first window, the light encounters the microporous membrane or film 6, which is deposited on the window and carries the indicator dye. There are several possible indicator dyes, e.g., bromocresol purple, bromothymol blue, thymol blue. As the light passes through this window, some of the light is absorbed into the indicator dye. The amount of light absorbed depends on the dye, the wavelength of the light, and the acidity of the gas flowing through the flow cell. The light, which has passed through the indicator formed by membrane or film 6 is transmitted through the second window 4 and falls on the detector 5, where it is measured.

Persons skilled in the art will recognize that the light source 1 and detector 5 may be constructed in several different ways. The light source may be monochromatic, emitting a single wavelength. If this is the case, the detector may be a simple light detector, e.g., a photodiode. It is also possible to use a light source with more than one wavelengths, e.g., several LED light sources optically combined. Thus it becomes possible to measure the absorption of the film on several wavelengths. Yet another variation is to use a broadband light source emitting several wavelengths at a time, e.g., a white incandescent bulb, and to use a colour detector instead of a simple light detector.

FIG. 2 illustrates a further alternative embodiment of a gas acidity measurement sensor. The second window 4 shown in FIG. 1 is replaced by a mirror 9, and the detector 5 is moved close to the light source. The advantage of this embodiment is twofold; the light 7 passes twice through the indicator 6, which doubles the signal, and there is no need for a second process window. This enables installing the instrument in a larger pipe or any other volume with gas 8.

Turning now to FIG. 3, the advantages of the previously mentioned embodiment can be achieved by using a window 3 with integrated porous mirror 10, i.e. this embodiment uses a porous mirror 10 disposed on the membrane or film 6. The integrated porous mirror 10 is for example a dielectric mirror comprising one or several porous layers. The dielectric mirror can be manufactured for instance of two materials having very differing refractive indexes. The film structure, i.e. pack film, can preferably be made to a multi-player structure, whereby the pack film should have at least three layers. It is especially preferable to form a pack in such way that it alternatively comprises a layer having a high refractive index and a layer having a low refractive index. A single layer of titanium oxide alone reflects about 20% of the incident light, but the reflection gets essentially better when layers are added. A five-layer pack provides a reflection of about 70% already. This mirror structure is described in U.S. Pat. No. 6,208,423 B1. This mirror structure allows the gas molecules to pass to the indicator film 6 while reflecting the light 7 backwards to the detector 5.

FIG. 4 illustrates a further alternative embodiment. The light source and detector are separated from the measurement sensor by using optical fibres 11 to carry the light. This makes it possible to move the light source 1 and detector 5 away from the measurement point. This may be desirable to, e.g., improve safety or otherwise remove the optoelectronic components from the vicinity of the gas.

In this embodiment, another change is introduced; the transparent plate 12 carrying the indicator layers 6 is immersed in the gas. In this construction it is possible to use an indicator film on both sides of the indicator plate. A further alternative is to use a solid piece of porous material with embedded indicator.

In all embodiments additional optical components, e.g., lenses, mirrors, image conduits, prisms, may be used to steer the light.

The embodiments of the invention described above are by no means intended to restrict the invention, but the invention can be modified completely freely within the scope of the claims. It is thus clear that for example the arrangement of the invention or its details do not necessarily need to be just like shown in the figures, but solutions of another kind are also possible. In other words, although the embodiments shown in the figures relate to several possible constructions for a gas acidity measurement sensor, various modifications and combinations of the embodiments as well as other embodiments of the invention will be apparent to those skilled in the art. It should be especially noted that by altering the indicator dye used in the invention, the sensor may be modified to measure oxygen, redox potential, or other chemical or physical property, which can be measured by colour indicators.

The invention claimed is:

1. A method of measuring acidity or other chemical or physical property of a gas, the method comprising:
    contacting a membrane having optical indicator molecules bound to a microporous matrix with the gas to be measured, the optical indicator molecules changing their color in response to the acidity or other chemical or physical property of the gas, and
    directing light to the membrane, whereby a part of the light is absorbed into the optical indicator molecules, and measuring the light passed through the membrane,
    wherein the light directed to the membrane has more than one wave length,
    wherein a porous mirror is disposed on the membrane and includes at least one layer allowing ions to pass through and reflecting light backwards to a detector.

2. The method according to claim 1, wherein the light directed to the membrane is a monochromatic light.

3. The method according to claim 1, wherein the membrane is deposited on an optical window of a flow cell containing the gas to be measured.

4. A system for measurement of acidity or other chemical or physical property of a gas, comprising:
    a membrane having optical indicator molecules bound to a microporous matrix arranged to be placed into contact with the gas to be measured, the optical indicator molecules changing their color in response to the acidity or other chemical or physical property of the gas,
    a light source, and
    a detector,
    the light source being arranged to emit and direct light to the membrane,
    wherein the membrane, light source and detector are arranged such that a part of the light is absorbed into the optical indicator molecules, and the rest of the light emitted is passed through the membrane and guided to the detector, where it is measured,
    wherein the light source is arranged to emit more than one wavelength,
    wherein a porous mirror is disposed on the membrane and includes at least one layer allowing ions to pass through and reflecting light backwards to the detector.

5. The system according to claim 4, wherein the light source is arranged to emit monochromatic light.

6. The system according to claim 4, wherein the membrane having optical indicator molecules bound to the microporous matrix is a dye film deposited on a substrate.

7. The system according to claim 6, wherein the membrane having optical indicator molecules bound to microporous matrix is a dye film fabricated by a Sol-Gel method.

8. The system according to claim 6, wherein the dye film deposited on the substrate is covered by the porous mirror.

9. The system according to claim 8, wherein the porous mirror is a dielectric mirror.

10. The system according to claim 4, wherein the membrane is deposited on an optical window of a flow cell for containing the gas to be measured.

* * * * *